I. L. PULVERMACHER.

ELECTRO-GALVANIC CHAINS, BANDS, &c.

No. 7,208. Reissued July 4, 1876.

Witnesses:

Geo. A. Turtchell

Will A. Dodge.

Inventor:

I. L. Pulvermacher, by Dodge & Son

Attys.

N. PETERS, PHOTO-LITHOGRAPHER, WASHINGTON, D. C.

UNITED STATES PATENT OFFICE.

ISAAC LOUIS PULVERMACHER, OF LONDON, ENGLAND, ASSIGNOR TO JOHN E. HETHERINGTON, OF CINCINNATI, OHIO.

IMPROVEMENT IN ELECTRO-GALVANIC CHAINS, BANDS, &c.

Specification forming part of Letters Patent No. 120,772, dated November 7, 1871; reissue No. 7,208, dated July 4, 1876; application filed April 28, 1876.

DIVISION B.

*To all whom it may concern:*

Be it known that I, ISAAC LOUIS PULVERMACHER, of London, England, have invented certain new and useful Improvements in Electro-Galvanic Chains, Bands, &c.; and I do hereby declare that the following is a full, clear, and exact description thereof, reference being had to the accompanying drawings, making part of this specification, and to the letters of reference marked thereon, like letters indicating like parts wherever they occur.

To enable others skilled in the art to construct and use my invention, I will proceed to describe it.

My invention relates to a single-liquid battery for constant currents, as hereinafter more fully described.

In carrying out my invention, I stamp a copper plate in such manner as to produce on one side thereof a series of projecting tongues, plates, or fillets, with slots or openings between them. I also stamp a zinc plate with a corresponding series of tongues, plates, or fillets, and slots or openings. I thus obtain, without loss of metal, open-worked plates having comparatively large acting-surfaces. I then bring the copper plate and zinc plate together, so that the projecting parts of the one may take between the projecting parts of the other, and I prevent metallic contact of the copper and zinc by interposing one or more thin strips or threads of india-rubber across the fillets. The copper and zinc are kept as close together as the india-rubber will permit, and the pair of plates constitutes one element of my battery. I suspend a number of these elements, so as to form a voltaic pile, or I connect a number of them together into a chain or band. The copper and zinc being open-worked, the exciting liquid, the gases, and the oxygen of the atmospheric air can circulate freely, and thereby contribute to the constancy of the current. Although I have mentioned copper and zinc as the metals I employ, any other electro-negative or electro-positive metal may be used.

Figure 1:
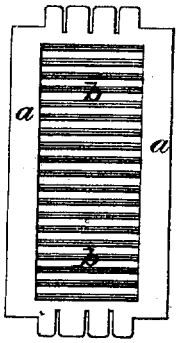
Figure 2:
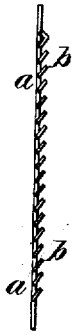
Figure 3:
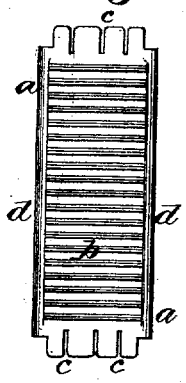
Figure 4:
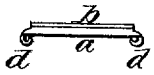
Figure 5:
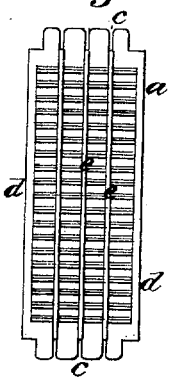
Figure 6:
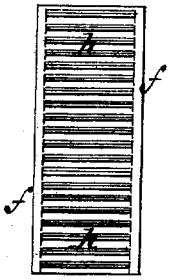
Figure 7:
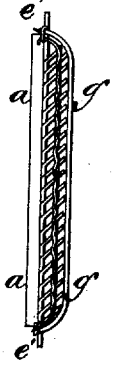
Figure 8:
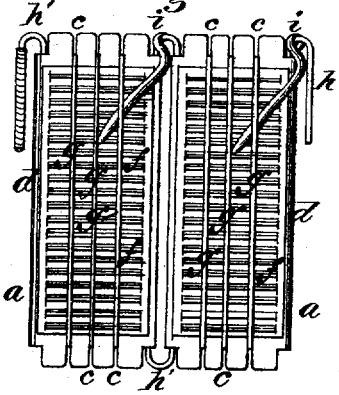

Figure 1 of the accompanying drawings represents in face view, and Fig. 2 in vertical section, a copper plate, *a*, stamped, as herein-before described, in such manner as to produce on one side thereof a series of tongues, plates, or fillets, *b*, with slots or openings between them. The plate *a* is also stamped with slits *c* at its ends. After being stamped with the projecting fillets *b* and slits *c*, the two sides of the plate *a* are rolled into the form of tubes *d d*, as seen in Figs. 3 and 4, which represent a finished copper plate, Fig. 3 being a face view, and Fig. 4 an end view. Threads of india-rubber are next placed in the slits *c* of the plate *a*, as shown at *e e*, Fig. 5, being secured therein by knots formed on their ends. Fig. 6 represents, in face view, a zinc plate, *f*, which has been stamped, like the copper plate *a*, with projecting fillets *h*, having openings between them. The copper plate *a* and zinc plate *f* are then brought together, as seen in section in Fig. 7, the plates being thus in close proximity; but metallic contact is prevented by the interposed rubber threads *e e*. The zinc plate *f* is held in place by other rubber threads *g g*, which are passed into the slits *c* and secured by knots *e′ e′*. The copper and zinc plates so connected constitute one element of the battery, any desired number of these elements being connected together to form a pile, or a chain or band. The manner in which I connect the elements is shown in Fig. 8, the elements being placed side by side, and bent copper pins or wires *h′ h′* being inserted, as shown, into the adjoining tubes *d d* of the elements, one leg of each of these pins being covered with an insulating material, so as to insulate the element into which it enters from that next adjoining. *i i* are wires establishing connection between the non-insulated portion of each pin *h′* and the zinc plate *f* of the adjoining element, as shown.

This mode of constructing or connecting the chains or piles is important, for if a chain be placed flat, with the zinc on the under side in a trough containing the exciting liquid, the zinc and the lower face of the copper will be wetted, but the upper face of the copper will remain dry, and its contact with the atmospheric air will permit of the copper producing a constancy of the maximum of its action by the depolarization of the air. It is hardly necessary to draw attention to the facility with which the zinc can be renewed, and to the certainty of its constant insulation from the copper by the interposed rubber threads *e e*, while the holding-threads *g g*, by their elasticity, always tend to force the zinc plate *f* toward the copper plate *a*.

Figure 9:
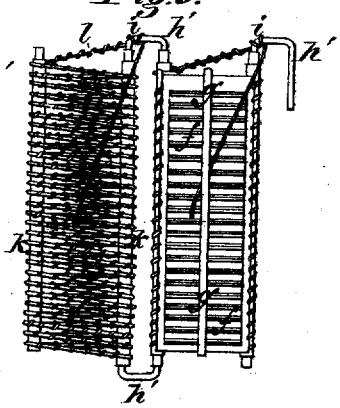
Figure 10:
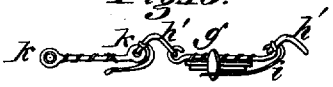

Figs. 9 and 10 represent a modified manner of forming the elements of my single-liquid battery. The zinc plate *f* is the same as before, and rubber threads *g* serve to hold the zinc plate in place, as in the previous case; but, instead of the open-work copper plate before described, I form the copper portion of the elements as follows: I take two copper tubes, *k k*, grooved or fluted externally and longitudinally, so as to cause the adherence of insulating-varnish with which they are covered. A cotton thread is then wound on the tubes from end to end, and they next receive a second coating of varnish. The two tubes are then held parallel to and at a suitable distance from each other by a copper wire, *l*, which is wound over them, passing from one tube to the other, in the form of an open spiral or flat helix, as shown. The wire *l* has wound around it previously, or at the same time, a cotton th ead, to prevent its contact with the surface of the zinc, which is placed against the copper part of the element and held by the threads *g*, as shown. The thread on this wire is wound on in an open manner, so as to leave a space between each spiral or turn for the exciting liquid to find access to the copper. The elements thus formed are then connected together by the bent copper pins or wires *h′ h′*, it being unnecessary to insulate one leg of these pins, because the required insulation is on the tubes *k k*. The top of these pins *h′* is bent at right angles, so as to allow the elements to dip into the trough containing the battery-liquid, while the tops of the pins rest on the partitions between the cells.

Having thus described my invention, what I claim is—

1. The plates *a* and *f*, having lips struck up or punched out of the metal thereof, substantially as and for the purpose set forth.

2. The plates *a*, having notches *c* formed in its ends for reception of the insulating and fastening cords or bands, as set forth.

3. The plate *a*, constructed as described, with the tubes *d* formed on its edges for the insertion of the hinge or connecting wires, as set forth.

4. The combination of the plates *a* and *f* with the insulating-cords *e* and the fastening-cords *g*, all arranged to operate substantially as described.

5. A galvano-electric chain or band, constructed substantially as shown and described.

ISAAC LOUIS PULVERMACHER.

Witnesses:

E. N. DANIEL,
166 *Fleet Street, London.*

J. S. ROBINS,
2 *Waterloo Place, Pall Mall, London.*